United States Patent [19]

Pratt, Jr.

[11] Patent Number: 4,941,474
[45] Date of Patent: Jul. 17, 1990

[54] MULTIVARIABLE ANALYSIS OF BONE CONDITION

[75] Inventor: George W. Pratt, Jr., Wayland, Mass.

[73] Assignee: Massachusetts Institute of Technology, Cambridge, Mass.

[21] Appl. No.: 214,184

[22] Filed: Jul. 1, 1988

[51] Int. Cl.$^5$ .............................................. A61B 8/00
[52] U.S. Cl. ................................ 128/660.01; 73/599; 73/602; 128/660.06
[58] Field of Search ..................... 73/597, 599, 602; 128/660.06, 661.03

[56] References Cited

U.S. PATENT DOCUMENTS 4,774,959 10/1988 Palmer et al. .................. 128/660.06

OTHER PUBLICATIONS

Larski, R. A. et al., "Computer Analysis of Ultrasonic Signals in Diffuse Liver Disease", UTS in Med. & Biol., vol. 5, pp. 341–359, Pergamon Press 1979.
Greene, F. M. et al., "Computer Based Pattern Recognition of Carotid Arterial Disease Using Pulsed Doppler Ultrasound", UTS in Med. & Biol., vol. 8, No. 2, pp. 161–176, 1982.
Greenfield, M. A. et al., "Measurement of Velocity of Ultrasound in Human Cortical Bone–in Vivo", Radiation Physics, Mar. 1981, pp. 701–710.
Bhagat, P. K. et al., "MP–based System for Ultrasonic Tissue Characterization", Med. Instrumentation, vol. 14, #4, Jul.–Aug. 1980, pp. 220–223.

Primary Examiner—Francis Jaworski
Attorney, Agent, or Firm—Wolf, Greenfield & Sacks

[57] ABSTRACT

A system for analyzing bone conditions, particularly (but not solely) for diagnosing osteoporosis and periodontal bone disease in humans. An ultrasonic signal (generally a pulse) having components in a range from about 50 kHz to about 600 kHz (and preferably to about 3 MHz) is launched transdermally into a bony member such as the patella, and received after passage therethrough. Scattering of the incident wave energy in the bony member, and absorption and phase delay in the tissue, cause the transmission to vary in both amplitude and phase as a function of frequency. A multivariable analysis is performed on a plurality of variables characterizing the signals transmitted through, reflected from or scattered by the bony member and soft tissue. The measured parameter values characterize the bone architecture and are compared with the statistics for one or more groups having known bone condition, to yield a probabilistic diagnosis of bone condition. The measured variables include the area, width at half power and peak frequency of the received power spectrum, as well as the second, third and fourth moments of the received spectrum, skewness, kurtosis and the propagation velocity through the bony member.

21 Claims, 7 Drawing Sheets

MULTIVARIABLE ANALYSIS OF BONE CONDITION

BACKGROUND OF THE INVENTION

1. Field of the Invention

This invention deals generally with diagnostic methods and apparatus for determining the condition of bones. In particular, it discloses a method for determining non-invasively, in vivo, the condition of certain bones in humans and animals. The invention is distinguished in part by the emission into the patient, adjacent a bony member, of a wideband ultrasound signal, and by the use of a multivariable analysis of the emerging ultrasound signal to analyze the architecture of scattering medium i.e., the bony member. The multivariable analysis may include a statistical study such as a multivariable discriminant analysis.

2. Discussion of the Problem and Objects of the Invention

This invention pertains to detecting bone disease and other abnormal gone conditions. The invention is intended specifically for evaluation and diagnosis of humans; but with obvious modification of the illustrative embodiments, the invention can be used to evaluate animal bones, also. Therefore, the term "patient" is used herein to include both human and animal subjects. The main object is to diagnose the presence of osteoporosis. However, other conditions may also be detected using this method, including bone condition variations following renal failure and periodontal disease due to bone deterioration. The invention may also be useful both for detecting fractures and for assessing, quantitatively, the healing of fractures.

The human skeleton is composed of tubular (long and hard) and cancellous (spongy) bones, each of which is composed of specific proportions of cortex (compact bone) and trabeculae (connective strands). Tubular bones, which are composed largely of cortex, dominate the appendicular skeleton that make up the limbs; cancellous bones, which are composed primarily of trabecular bone, dominate the axial skeleton of the vertebral column and pelvis.

In both cortical and trabecular bone, the collagen fibrils extend throughout. The difference between the two is actually one of degree, depending upon the form the network of collagen fibrils takes. In general, the fibrils may be separated such that the network is a network of rods. They may also be more closely spread, so that the network appears as a network of plates connected by rods. In both cases, a certain volume of the bone will comprise mineralized collagen fibrils, and a certain volume will comprise non-osseous material known as "marrow."

Whether a particular bone assumes a trabecular or cortical formation is thought to depend largely upon the function that bone serves. The method of bone formation is not well understood; however, it is believed that the process of bone accretion responds in some manner to stresses experienced by the bone. Therefore, that region of a bone that experiences relatively high stresses, such as the diaphysis of the tibia of the leg, tends more toward cortical bone. Regions of a bone that experience low stress tend more to be trabecular. In most sites of trabecular bone, the trabecular mass is surrounded by a relatively thin layer of cortical bone. The patella is mostly trabecular with a subcortical layer just beneath the anterior surface.

As used herein, "patella" refers to the thick, flat triangular bone that forms the anterior part of the knee; "kneecap" refers to the patella and surrounding soft tissue; and "tibia" refers to the anterior bone of the lower leg.

The principal target of the invention (that is, the primary condition for which diagnosis is sought), osteoporosis, is a disease of unknown cause which afflicts people, generally, as they age. Osteoporosis afflicts women more often than men; and of women, more often after menopause. White women are more often stricken than women of other races. Osteoporosis is manifest as an absolute decrease in bone tissue mass. The bone that remains is, however, normal. A person suffering from osteoporosis loses a greater proportional amount of trabecular bone than cortical bone.

Another target of the invention, periodontal disease, involves loss of bone in the mandible and maxilla, with consequential loosening of teeth. Heretofore, the progress of bone loss in the jaw has been monitored with X-rays, which can only reveal the presence of periodontal disease after substantial bone loss has already occurred.

Consequently, it is highly desirable to provide a means for detecting bone condition (and, hence, changes in bone condition—including, but not limited to the loss of bone material and attendant decrease in bone density and elasticity). Optimally, such means is non-invasive, accurate, sensitive, easy to use and can be made generally available. This is not, however, true of the prior art techniques, in general.

In recent years, several methods have been proposed for the early diagnosis of osteoporosis. These methods include Neutron Activation Analysis of Total Body Calcium (TBC), single photon aborptiometry (of wrist and os calcis) and dual photon aborptiometry (of the spine and neck of the femur), Computer Aided Topography (CAT scanning) and methods of ultrasound analysis. The advantages and disadvantages of these techniques are well documented in the literature and are summarized in commonly assigned U.S. patent application Ser. No. 06/870,175, filed June 3, 1986, titled "Ultrasound Method and Apparatus for Evaluating, In Vivo, Bone Conditions," which is incorporated by reference herein in order to avoid needless repetition.

For in vivo, non-invasive analysis of bones in patients, measurement by use of ultrasound already has been performed to some extent. Ultrasound measurement, however, is complicated, in part, by the presence of soft tissue surrounding most bones. The propagation speed of an ultrasound signal injected transdermally is affected by passage through the soft tissue surrounding the bones, as well as by passage through the bone(s) of interest. It is possible to minimize the effect of the soft tissue. Initial attempts to minimize the effect of the soft tissue were encumbered by requirements for rather sophisticated echo analysis and careful measurement. See, for example, U.S. Pat. No. 4,361,154, "Method for Establishing, In Vivo, Bone Strength." A more advanced system is presented in U.S. patent application Ser. No. 06/870,175, filed June 3, 1986 in the names of George W. Pratt, Jr. and Paul Duchnowski and titled "Ultrasound Method and Apparatus for Evaluating, In Vivo, Bone Conditions." That system employs an ultrasonic pulse having at least two components of distinguishable waveshape or frequency content in a range from about 100 kHz to about 3 MHz, launched transdermally through a bony member such as the patella. A variety of techniques are used to distinguish between the signal transmitted by the soft tissue and the signal transmitted by the bone, to facilitate assessment of bone condition. These techniques include comparing the transit times through the bony member of energy in a first frequency range and energy in a second frequency range; evaluating the transfer function through the bony member of the portion of the signal travelling through the bony member; evaluating a gain function of the power spectrum of the portion of the signal transmitted through the bone, including evaluation of the area under such gain function and/or the magnitude and location of its peak amplitude. The gain function whose area was evaluated was the absolute value squared of the system function, the latter being defined as the received signal normalized by the transmitted signal—i.e., the transfer function of the channel existing between the two transducer faces. Such prior application also teaches the deduction of velocity of ultrasound energy through the bony member by determining the duration of travel of the ultrasound signal through the bony member and soft tissue, and adjusting such composite velocity by a soft tissue normalization factor. This information is then compared to a database of prior measurements for the same patient and/or for a selected population (which may be, for example, the population at large or a selected population of like age, sex, race, etc.), to determine a probability that the patient s bone condition is abnormal.

The techniques of that previous application represent a significant improvement over the prior art, but they still have left room for further improvement. The measurements based on signal transit time and velocity are sensitive to transducer orientation and placement, for example. The gain function evaluations show promise but do not provide a basis for an individual diagnosis having the degree of confidence physicians demand.

The principal object of this invention, therefore, is to provide a superior method and apparatus of ultrasound diagnosis of bone condition.

This broad object may be formulated in several other ways and in subsidiary and related objects: (1) to evaluate bone condition in patients using a non-invasive, in vivo technique; (2) to evaluate bone condition without subjecting patients to substantial doses of ionizing radiation; (3) to evaluate bone condition in patients economically and quickly; (4) to provide a method or methods of evaluating bone condition that may be performed safely and economically many times over the course of several years; and (5) to provide a method or methods of evaluating bone condition that may be performed by a technician without the need for expensive equipment or especially careful transducer placement or measurement.

SUMMARY OF THE INVENTION

Broad Overview

According to the present invention, bone (or a bony member) and, in particular, trabecular bone is modelled at least in part as a scattering medium (wherein the scattering may, but need not, be Rayleigh scattering). Bone condition is determined by sending into the bone (more precisely, a selected bony member) an ultrasound signal (preferably, but not necessarily, one having an amplitude which varies substantially linearly with frequency) and extracting from the ultrasound signal received after passage through the bone a number of parameters, including parameters identifiable with the scattering model and characterizing the bone architecture and the received signal's signature. A statistical model is built, using these parameters for a group of patients whose bone condition is known by other reliable methods. Once the statistical model is available, the parameters extracted from an individual patient are compared with the model built from patients whose bone condition is known, using a multivariable analysis such as a discriminant analysis, pattern analysis or signature analysis, to arrive at a probabilistic diagnosis of the patient's bone condition.

More Detailed Overview

The emitted ultrasound signal preferably contains a continuous or substantially continuous spectrum from about 100 kHz to about 500–600 kHz and may have components extending up to about 2–3 MHz. The amplitude of the emitted signal should preferably not be constant over the 100–600 kHz range; a linear variation of amplitude with frequency has been found to be superior, and other non-flat spectra may be used, as well. In the absence of a continuous spectrum, the invention may be practiced with a plurality of narrow-band signals. The signal or signals may be in either pulse or continuous-wave format, or some combination thereof. Hereinafter, except as expressly appears otherwise, where the term "pulse" is employed, it is intended to include both finite duration and continuous-wave signals. If narrow-band signals are used, they may be transmitted at the same time (e.g., as part of a composite waveform) or at different times.

The invention relies on the observation that the transmission of an ultrasound signal through bone is frequency-dependent, and that the details of the frequency dependence contain clues to the condition of the bone. The frequency dependence of the transmission properties apparently is due to the scattering of sound out of an incident beam. More particularly, the invention at least in part exploits the discovery that bone (at least trabecular bone) can be modelled as a Rayleigh scattering medium for a large range of ultrasound signals.

From the frequency-dependent propagation characteristics through the bone, the values of the parameters of the Rayleigh-scattering model are derived. These parameters yield information about the bone architecture, such as the average size of the non-osseus volumes in the bone.

Several modes of operation are available in accordance with the invention. In a first mode, called the reflection mode, only one transducer is employed for both sending and receiving the ultrasound signal. In the reflection mode, the single transducer sends the ultrasound signal into the bone and then receives the echoes from the bone, the echoed signal being used as the diagnostic signal. In a second mode, called the transmission mode, a pair of transducers is used; one serves as the sending transducer and the other as a receiving transducer. In the transmission mode, a longitudinal wave is transmitted into the bone by the sending transducer, the wave travels through the bone toward the receiving transducer, and it is received by the receiving transducer which converts it into an electrical signal. In a third mode, called the scattering mode, an input wave is launched at the surface of the bone; upon hitting the bone, the acoustical energy travels through and is continually scattered in the bone. A second transducer which is not parallel to the first transducer receives the scattered waves and the received signal is then analyzed.

In all three modes, of course, while the acoustic wave transits the bone it is subject to scattering.

The sending and receiving transducers are connected to an ultrasound pulse generator and to a signal receiving and processing system, respectively.

In the transmission mode, the bone to be measured preferably is surrounded by only minimal soft tissue and its surface preferably has opposing portions and sound energy may be coupled into and out of these portions by faces of sending and receiving transducers arranged substantially in parallel.

In the reflection mode (sometimes called the echo mode), the single transducer for sending and receiving is positioned so as to direct its ultrasonic energy into a bony member (preferably having only a minimal soft tissue covering) and so as to receive the echo that arises from scattering of the ultrasound signal within the bone itself.

In the scattering mode, the positions of the transducer faces may be varied relative to the bony member, so long as the faces are not parallel on opposite sides of the member.

In those cases where a first part of the received signal travels primarily through soft tissue alone and a second part travels through both bone and soft tissue, the received signal preferably is processed (a) to separate said first and second parts, so as to distinguish the effect of the bone from the effect of the soft tissue and (b) to obtain from the second part information suggestive of the properties of the channel (i.e., bone) through which it has passed. This is done by exploiting the differences in propagation of the first and second parts, in the time and frequency domains. For example, the speed of sound is slower in soft tissue than in bone and experiences much lower attenuation at higher frequency in soft tissue than in bone. Hence, in the transmission mode, for example, late arriving, high frequency signals can often be classified as being dominated by soft tissue propagation. The received "bone" signal is processed and certain variables are extracted which characterize its frequency-dependent propagation and scattering. The processing of the received signal may be performed directly on the received signal or only indirectly on the received signal. Indirect processing of the received signal involves, for example, processing of the system function, transfer function or gain function, or the processing of the Fourier transform, z-transform, power spectrum, or some other transform of any of those functions, and the subsequent extraction of variables characterizing the frequency-dependence thereof.

The step of processing the received signal to distinguish the bone signal from the soft tissue signal further may involve determining the ratio of the time of arrival of the bone signal to the time of arrival of the soft tissue signal. This ratio is proportional to the ratio of the velocity of sound in bone to that in the soft tissue, but is insensitive to distance measurements.

The selected combination of factors is compared with the statistics for a collection of such data for patients previously diagnosed, using a multivariable discriminant analysis, to yield a probability (or set of probabilities) that the patient's bone has (or is in) a particular condition(s). This probability will provide a diagnosis of osteoporosis with far greater accuracy than any prior non-invasive technique.

To determine the ratio of the velocity of the bone signal to the velocity of the soft tissue signal, the matched filtering/Fourier transform filtering techniques and apparatus of the aforesaid application Ser. No. 06/870,175 are used. To avoid unnecessary repetition, the specification of application Ser. No. 06/870,175 is hereby incorporated by reference herein.

Various bone sites may be used for test purposes, but the kneecap has been found to be a favorable location due, in part, to the fact that (a) the distance through the soft tissue layers surrounding the patella is much less than the distance through the bone and (b) in the transmission mode there exists an acoustic propagation path through the soft tissue transducer, overlaying the patella which is approximately parallel to, or nearly the same distance as, the propagation path through the patella and soft tissue layers.

The foregoing, and other as yet unstated, objects and advantages and features of the invention will become more apparent from the following detailed description and the claims appended thereto, all of which should be read in conjunction with the accompanying drawing.

DETAILED DESCRIPTION

Figure 1:
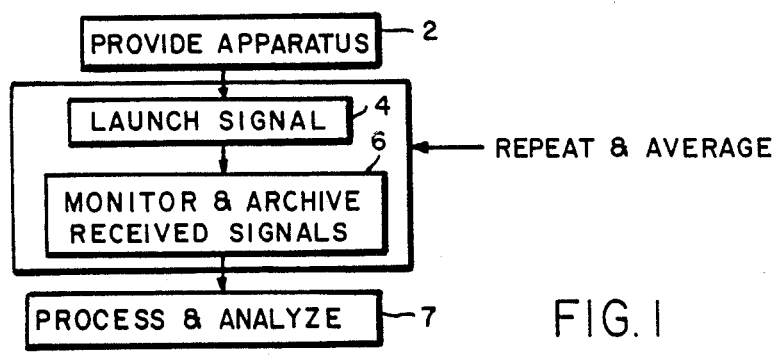
FIG. 1 is flow chart outlining in general the steps of the method of the present invention.

Turning to FIG. 1, a schematic flow chart illustrates the basic steps of the method. The first step, of course, labelled with the numeral 2, entails providing an appropriate apparatus to conduct the generation, administration and measurement of ultrasonic signals. The apparatus, which will be discussed more fully below in connection with FIG. 3, consists generally of an ultrasonic signal generator, a pair of transducers for use in the transmission or scattering modes or a single transducer for use in the echo mode, and a signal detection and analysis unit. For ease of discussion, the ultrasonic signal provided by the ultrasonic generator will hereafter be referred to as a "pulse" regardless of the exact waveform of such signal. Thus, a pulse will simply mean the signal that excites the sending transducer and whose amplitude, frequency content, duration and repetition rate are preselected.

Figure 2:
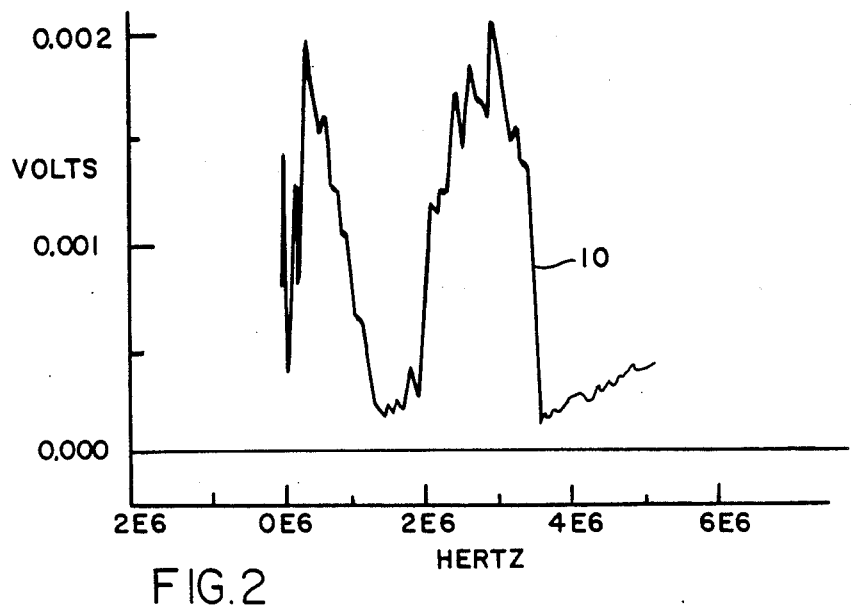
FIG. 2 is an illustration of the spectrum of the ultrasound signal emitted from a typical transducer found to be useful in the apparatus of FIG. 3.

As indicated in block 4, a broad-band waveform generator can be used to launch from the sending transducer a sound pulse containing energy components from about 50 kHz to about 3 MHz, for a duration of approximately $5 \times 10^{-6}$ seconds. The signal amplitude and power may vary widely over that spectrum, as shown in FIG. 2, which illustrates the spectrum 10 of the excitation. As a first-order approximation, the transmitted signal may be considered a "ramp" within the frequency band of interest—i.e., the transmitted signal amplitude $V(\omega)$ has a frequency dependence $V(\omega) = V_o \omega$, where $\omega$ is the angular frequency, in radians. The launching (i.e., its time-dependence) of the pulse is recorded by a data acquisition system, which stores it on a magnetic disk or other archivable medium. The launched pulse may also be displayed on a cathode ray tube or other suitable display device. The next step, 6, includes monitoring acoustic excitations at the receiving transducer to detect the signal passing primarily through the bone, regardless of mode. Step 6 also includes the operations of generating electronic signals in response to the detected acoustic excitation, storing a record of those signals by means of the data acquisition system, and (if desired) displaying the record of those signals on the same cathode ray tube display. In step 7, the received signals obtained from step 6 are processed (by a variety of techniques, which may include analog or digital filtering, Fourier transform analysis, z-transform, chirped z-transform, matched filtering, and a variety of other computations) to extract one or more derived measurements and parameter values characterizing the received signals. These derived measurements and parameter values may then be compared with the statistics for comparable data characterizing patients having known normal and diseased bone conditions, using a multivariable analysis (e.g.. a multivariable discriminant analysis or cluster analysis), to obtain a diagnosis. The statistical evidence, or model, characterizing the patients of known condition (e.g., normal and osteoporotic or otherwise diseased) can be refined by including factors such as age, height, weight, velocity characteristic, race, ethnic group, and so forth). The multivariable discriminant analysis selects weightings for each factor, as derived from the statistics. Using these weightings, the analysis yields, for each condition represented, a probability that the patient's condition matches the evaluated condition. For example, if each patient of known condition has been categorized as having one of two conditions—e.g., as being osteoporotic or normal, the discriminant analysis yields for the patient of unknown condition a probability that such patient is osteoporotic and a probability that such patient is normal. One can then choose to diagnose a patient as osteoporotic when the probability of osteoporosis is greater than a selected threshold value. The normal and osteoporotic groups may have fine structure defining additional conditions which may be recognized by techniques such as cluster analysis—e.g., the osteoporotic group may actually include victims of both osteoporosis and osteopenia.

Diagnosis of bone condition using ultrasound is made possible by the fact that the patient's soft tissue and bone act like a complex network, transmission channel or filter with propagation properties varying as a function of frequency. A number of these transmission properties are due to the physical condition (i.e., architecture) of the bone itself. The resulting alteration of the ultrasound signal waveshape as it passes through the patient thus provides, at the receiving transducer, a very much altered spectrum. An evaluation of the characteristics of the received spectrum by either analog or digital processing means, yields information about the condition of the patient's bone.

It is good practice, although not essential, to reduce error due to random noise by repeating steps 4 and 6 several times and averaging the results.

The many transformations of the ultrasound excitation which occurs as it propagates through the patient are not yet fully understood. Present indications are that for the patella, in the transmission mode, within the frequency spectrum of interest, the higher frequency components travel as a leakage mode through the soft tissue covering of the bone and that the lower frequency components propagate along a parallel path in the bone. More particularly, with respect to the patella, the lower frequency signals appear to propagate in the bone underlying the soft tissue leakage path. This bone path sharply attenuates the high frequency content of the applied ultrasound pulse. The nature of the propagation through the bone is affected by the scattering of the incident acoustic energy by non-uniformities in the bone. Moreover, that scattering is further affected by the size and number of these scatterers. At least part of the scattering can be attributed to Rayleigh scattering. In the echo mode, the transmitted signal is reflected by any boundary encountered for which the acoustic impedance differs between the materials on the sides of the boundary. Once again, the incident sound waves are scattered by non-uniformities. A portion of this scattered signal is reflected and can be picked up by the single transducer as an echoed signal. Later arriving echoes come from regions further away from the transducer face. Thus echoes from different parts of the bony member can be distinguished by proper choice of the arrival time of the echo signal to be examined.

Figure 3:
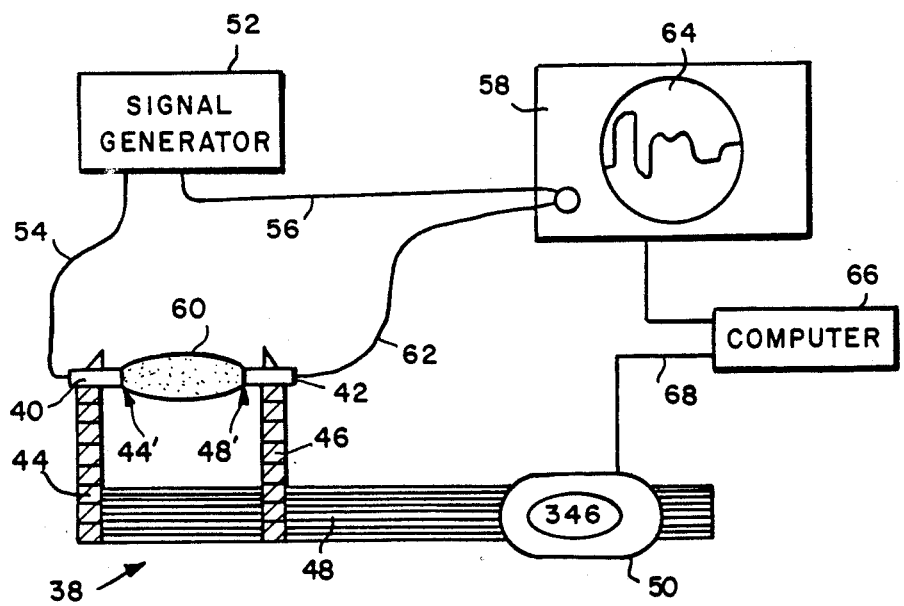
FIG. 3 shows a schematic representation of an apparatus that may be used to practice the method of the invention in the transmission mode.

With reference now to FIG. 3, a suitable apparatus for practice of the invention will be described in detail In the transmission mode, transmitting and receiving transducers 40 and 42 are mounted on a digital caliper device 38 or other assembly which maintains the transducer faces in a repeatable spaced relation. Preferably the transducer faces are maintained parallel to each other. The transducer faces are closed about the bony member to be evaluated, until they are in contact with the patient's surrounding skin. The coupling of ultrasound energy between the transducers and the tissue may be facilitated by an impedance matching gel or similar substance. As the excitation is being launched and received, the caliper automatically measures the distance travelled by the pulse (i.e., the separation between the opposing faces of the transducers). Both the transmitted and received signals are recorded, as a function of time. Using techniques described below and in the specification of U.S. patent application Ser. No. 06/870,175 (which has been incorporated by reference), the received signal is processed to extract therefrom the signal which was transmitted through the bone itself: that is, the effect of the surrounding soft tissue is, to a substantial degree. removed.

After the transmission and excitation data have been recorded, it is necessary to determine the time of arrival of the signal propagating through the tissue-covered bony member. A preferred technique is that of matched filtering wherein a template signal representing the signal sent into the bone is provided, which is matched through a cross-correlation function to the signal corresponding to the excitation at the receiving transducer. Evaluation of the cross-correlation function permits filtering out the noise making up the baseline signal, thereby facilitating pinpointing the exact time of arrival of the pulse. This technique is known as matched filtering. Once both the elapsed time of pulse travel and the distance travelled are known, the average velocity of the ultrasound pulse through the bone and surrounding soft tissue can be computed.

Having determined the time of arrival of the bone signal, it is necessary to then isolate or identify a portion of the response that comes principally through bone alone. For example, if the first arriving signal occurs at $T_1$, then a tissue signal propagating along a substantially parallel path through soft tissue can be expected to arrive at $T_2 = T_1(V_{bone}/V_{tissue})$, where $v_{bone}$ and $v_{tissue}$ are, respectively, the propagation velocities of the ultrasound signal in bone and in soft tissue. Using average values for $v_{bone}$ and $v_{tissue}$ (e.g., 2000 m/sec and 1540 m/sec, respectively), $T_2$ can be estimated. Thus the signal arriving from $T_1$ to $T_2$ comes primarily through the bone.

The spectral properties of the bone signal are analyzed to assess the condition of the bone. The ratio of the velocity of ultrasound propagation through the bone to the velocity of ultrasound propagation through the soft tissue also mag be used in conjunction with a spectral analysis, as hereinafter described.

Each transducer (40 and 42) is capable of launching a broad band high frequency ultrasound pulse. Transducers manufactured by Panametrics Inc., 221 Crescent St., Waltham, Mass. 02254, such as the Panametrics model A533S transducer, have been used with good results. The spectrum of the signal emitted by the above-described transducer contains substantial energy components from about 100 kHz to about 3 MHz. This broad spectrum is desirable, as the signal transmitted through the bone has significant energy at frequencies in the neighborhood of 250 kHz, while the signal transmitted through soft tissue has significant energy at frequencies in the neighborhood of 2.5 MHz. Additionally, I believe, satisfactory results may in at least some situations be obtained with a spectrum limited to an upper frequency of a few hundred kilohertz.

The workings of caliper 38 are unimportant to the disclosed invention, and an ordinary vernier caliper also could be used. However, in that case, manual readings of the distance would have to be taken, and the distance would have to be read into the data processing equipment by hand. A digital caliper is just a labor-saving device. In the transmission mode, the sending transducer 40 and receiving transducer 42 are brought to bear upon opposite surfaces of a bony portion of the patient's body 60, preferably the kneecap. The signal generator 52 generates a pulse of a duration of approximately $7 \times 10^{-6}$ seconds. This pulse is transmitted along electrical connection 54 to the launching transducer 40. Simultaneously, along electrical connection 56, a launch signal is transmitted to the data acquisition system 58, indicating the departure of the launched pulse.

The pulse travels through the member being measured 60 and is received by the receiving transducer 42. The receiving transducer 42 emits responsive signals that are electrically transmitted along lead 62 to the data acquisition system 58.

The data acquisition system 58 is capable of storing the signals received by it, and displaying the time-varying amplitude upon a standard CRT display 64. The data acquisition system includes data computing means 66, shown schematically in FIG. 3. A signal representing the distance measured by the caliper 38, between the transducer faces 44' and 46', has been transmitted along electrical connection 68 to the computer 66, for use at a later step as described below.

Figure 4:
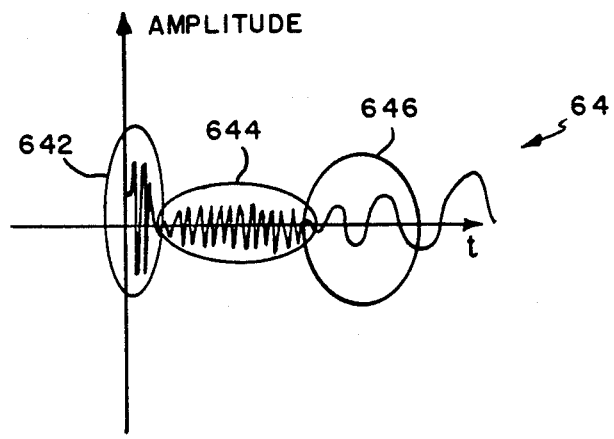
FIG. 4 is a diagrammatic illustration of the received signal generated by the receiving transducer of FIG. 3, in the transmission mode.

The next figure, FIG. 4, shows schematically a typical response received by the receiving transducer. In FIG. 4, the display is represented by 64. The horizontal axis represents elapsed time. The time from the origin to the end of oval 644 is on the order of 15 to $20 \times 10^{-6}$ seconds. The vertical axis represents the amplitude of the signal received.

The portion of the signal indicated within the circle identified as 642 shall be referred to as the "main bang" and constitutes the record of the launched pulse. The portion of the signal roughly circumscribed by oval 644 is the base line noise received by the receiving transducer. The portion of the signal indicated by oval 646 represents the initial receipt by the receiving transducer of any signal passing through the bone and soft tissue as a result of the launched pulse. This received signal consists of two distinguishable components: a first arriving low frequency signal followed by a later arriving high frequency signal, not shown. These signals may also be termed, respectively, a "received first distinquishable component" and a "received second distinguishable component". To more readily extract the signal from noise, well-known techniques of spectral estimation may be used. These techniques are discussed in many texts, such as S. M. Kay, *Modern Spectral Estimation: Theory and Application,* Prentice-Hall, 1987, which is hereby incorporated by reference. For example, the amplitude and/or power spectrum of the received signals from a number (e.g., 16 or more) of separate, initial pulses may be averaged; random signals, such as noise, tend to average to zero.

As can be seen from the schematic representation in FIG. 4, it is difficult to determine precisely the time at which the signal 646 emerges from the baseline noise 644. Errors in determining the time or arrival by as much as $1 \times 10^{-6}$ seconds can result in an error in the velocity calculation of as much as 10 percent. Although measurements made with an error of this amount will still be useful, it is, of course, highly desirable to eliminate (or, at least, minimize) this error to the extent possible. Fortunately, a method has been developed for correcting for errors of this type. This method is know as "matched filtering." It is described in full in various texts, such as Y. W. Lee, *The Statistical Theory of Communication*, published by Wiley in 1960. This matched filtering need not done at the time of patient examination, and may be performed later, on stored data.

After the elapsed time for the signal propagation has been determined as outlined above, the velocity may be computed by dividing the distance between the transducers (measured earlier), by the elapsed time.

Once the average velocity through the path between the transducers has been determined, it is beneficial to isolate the bone signal by removing the effect of the passage of the ultrasound pulse through the soft tissue surrounding the bone, as taught in application No. 06/870,175 or as taught above.

When wide-band excitation is employed, the low frequency oscillations and the high frequency oscillations from the transmitting transducer arrive at different time at the receiving transducer. These signals may be separated using known techniques such as those shown in application No. 06/870,175.

In accordance with the teachings of application Ser. No. 06/870,175, one parameter of the bone signal which has been found to be a good indicator of bone condition is the area under the magnitude of the Fourier transform of the bone signal up to a limit of about 500 or 600 kHz. In an experimental study, the average area measurement for eight osteoporotics was 15.71 units, with a standard deviation of 6.35; by comparison, the average for twelve normal patients was 41.56 units, with a standard deviation of 19.99. This demonstrates the viability of using some type of spectral analysis measure for diagnostic purposes, but it also demonstrates that the chance of a misdiagnosis is still significant with that method.

One step which facilitates reliable diagnosis is to test the received signal to determine if the acoustic cougling between the transducer face or faces and the bony member is sufficiently strong so that the first arriving bone signal may be reproducibly recognized from the background noise. A test which appears satisfactory is to evaluate the area under the magnitude of the received bone signal. A signal is acceptable if that area is of sufficient size so that the recognition process is reliable; a numerical value can be assigned to the threshold area which depends on the transducer size, the pulser and the receiver, etc.

Further spectral study of the received signals has revealed that the frequency-dependent attenuation of the input ultrasound signal as it travels through the bone appears to be at least partly due to scattering of the wavefront from scattering sites in the bone. The principal scattering mechanism may be due either to the marrow-filled interstices (referred to as "cells" or "voids") or to the bony network, as determined by the architecture of the bone under study. Such transmission loss appears to be characterized to a significant degree by a Rayleigh scattering model. The cells in the trabecular bone can be modelled as spherical in shape, with a typical diameter of about 1 mm. The wavelength of sound, by contrast, is about 1 cm. Thus the condition for Rayleigh scattering is fulfilled; that is, the wavelength is large compared to the radii of the scatterers.

Assuming an idealized representation (which may or may not be medically significant), the bone may be modelled as a Rayleiqh channel having an attenuation constant per unit length, $\alpha$. The power loss from the incident ultrasonic beam is then given by the expression $$\alpha = \frac{P_L}{2 P_T}$$

where $P_L$ is the power lost per unit length and $P_T$ is the incident power transmitted. The power lost per unit length, $P_L$, is the power scattered per individual scatterer, $P_s$, times the number N of scattering elements per unit volume. According to G. S. Kino, *Acoustic Waves*, Prentice Hall (1987) at 313, the total scattered power $P_s$ of ultrasound energy of propagation constant "k"=$\omega/c$, due to a single scatterer of radius "a", is given by the relationship $$P_s = \frac{7\pi k^4 a^6 I_i}{9}$$

where $I_i$ is the incident intensity. The incident power, $P_T$, is given by $$P_T = I_i A$$

where A is the area through which the sound enters the bone. The total loss per unit length, $P_L$, is $P_s NA$, where N is the number of scatterers per unit volume. Hence, $$\alpha(\omega) = \frac{7\pi N \omega^4 a^6}{18 v^4}$$

The power spectrum transmitted through a length L of bone is $$P(\omega, L) = P_i(\omega) e^{-\alpha(\omega)L}$$

where $P_i$ is the incident power.

Of course, the incident transmitted power $P_i$ may vary with frequency in some arbitrary manner, as the spectrum Pi($\omega$). The received power (or voltage) will then vary in some related manner. While it will be readily understood that this analysis can be performed for such an arbitrary $P_i(\omega)$, to simplify the signal processing, assume that the amplitude of the voltage at the sending transducer, $V_i(\omega)$, can be approximated over the frequency range of interest (i.e., the range transmitted by the bone) as:

$$V_i(\omega) = V_o \omega^n,$$

where n is an integer. It has been found that a value of unity for n is advantageous. This is a reasonable approximation in view of the waveform of FIG. 2. Since the power varies with the square of the received voltage, the incident power is, for n=1, $$P_i(\omega) = P_o \omega^2$$

The received voltage in the frequency domain is $$V(\omega,L) = V_o \omega e^{-\alpha(\omega)L/2}$$

The frequency at which the received voltage peaks is thus given by $$\omega_{max} = \left[ \frac{36v^4}{28\pi Na^6 L} \right]^{\frac{1}{4}}$$

For the patella, we may use the following values: $v = 2.2 \times 10^5$ cm/sec, $L = 5$ cm, and $a = 0.05$ cm. N is given as the porosity p divided by the volume of the average scatterer. Taking $p = 0.67$ for trabecular bone, N is approximately $1280$ cm$^{-3}$. This yields a predicted frequency of peak response, $f_{max} = \omega_{max}/2\pi$, at 280 kHz. Experimentally, with a group of 100 signals from 25 osteoporotics, the average peak frequency was found to be 254 kHz. With 64 signals from 16 normal patients, the average peak frequency was, by contrast, found to be 267 kHz. In view of the numerical assumptions made above, this is a very satisfactory agreement. Thus, the peak frequency of the response is a useful indicator of the patient's bone condition. The received voltage from that portion of the transmitted, scattered or reflected signal due primarily to propagation through bone is isolated from the total received voltage signal in the time domain, and then Fourier transformed to produce the frequency domain signal. The step of isolation can be carried out in several ways. One simple means, when the transmitted signal is in the form of repetitive pulses, is to recognize the time of arrival $T_{bone}$ of the bone signal as the start of the bone signal, and take the end of the bone signal to be 1.4 $T_{bone}$, where 1.4 is approximately the ratio of $v_{bone}/v_{tissue}$. Another method for isolating the bone signal is described in the above-referenced patent application no. 06/870,175.

Other parameters and measurements related to the bone signal have been identified as indicators of bone condition. When a combination of such factors is employed, the statistical degree of confidence in the diagnosis is quite high. Though many spectral parameters may be considered, the most significant parameters appear to be: the peak frequency $f_{max}$ or $\omega_{max}$, the full width of the received spectrum at half power (FWHM), and the moments $M^n(\omega)$ of the received spectrum where the $n^{th}$ moment $M^n(\omega)$ is given by $$M^n(\omega) = \frac{\int_0^F (\omega - \overline{\omega})^n H(\omega) d\omega}{\int_0^F H(\omega) d\omega}$$

and $$(\omega) = \frac{\int_0^F \omega H(\omega) d\omega}{\int_0^F H(\omega) d\omega}$$

in which $H(\omega)$ is the amplitude of the Fourier transform of the bone signal or another function of the frequency dependence of the received signal and F is the upper frequency limit of the bone signal. Such other function could, for example, be the power spectral density, system function or gain function. Moment functions such as skewness and kurtosis have also proved useful. Skewness, of course, is defined as $M^3(\omega)/[M^2(\omega)]^{3/2}$ and kurtosis is defined as $M^4(\omega)/M^2(\omega)^2$. The ratio of the velocity of the bone signal to the velocity of the soft tissue signal may optionally be considered in conjunction with these factors.

From the Rayleigh scattering model, the scattering cross-section varies as the 4th power of the frequency and as the 6th power of the radius of the scatterers. This sixth power dependence makes the attenuation due to scattering quite sensitive to the architecture of the bone, which is, of course, what one seeks to determine in diagnosing osteoporosis. The velocity of sound varies as the square root of the elastic modulus divided by the density. The modulus varies as the density raised to a power between two and three. Thus, velocity measurements alone are less sensitive to the condition of the bone than are appropriate, selected spectral measurements. In combination with the selected spectral parameters, though, velocity measurements increase the quality of the prediction of bone condition. This can be seen from the expression for $\omega_{max}$, which varies as the velocity divided by the fourth root of $28\pi Na^6 L$. Thus $$\frac{\omega_{max} L^{\frac{1}{4}}}{v}$$

is proportional to the fourth root of the product of the porosity and the volume of the Rayleiqh scatterers.

Figure 5:
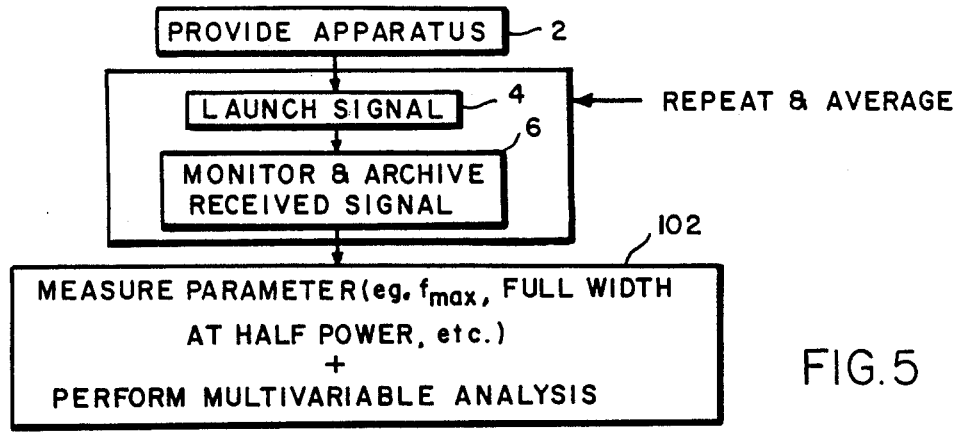
FIG. 5 is a flow chart outlining in greater detail the implementation of step 7 of FIG. 1 as a sequence of more specific steps according to an embodiment of the method of the present invention.

Referring to FIG. 5, the method of the invention is shown in greater detail. Once the various data are available, a multivariable discriminant analysis is performed (step 102) to compare this data with the statistics for individuals whose bone condition is known.

Figure 6:
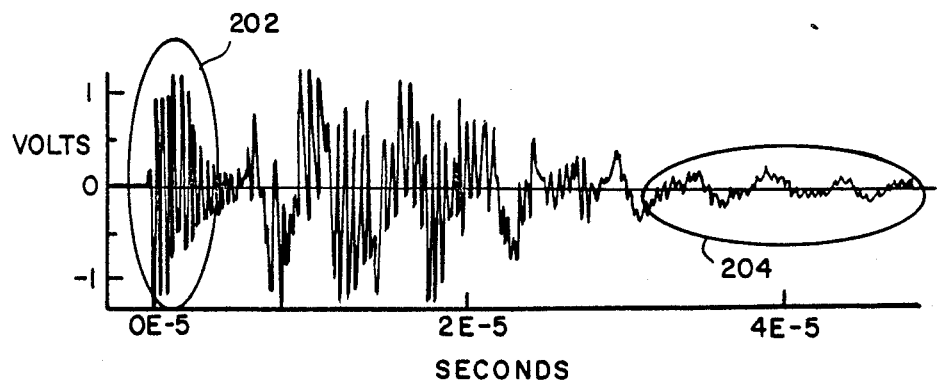
FIG. 6 is an illustrative example of the received signal according to the present invention when the invention is operated in the reflection mode to evaluate a patella.

In the reflection mode, a single send-receive transducer alternately emits an ultrasound signal and listens for echoes. The return signal, or echo, from reflection of a transmitted signal directed substantially normal to the face of the patella is shown in FIG. 6, where signal amplitude is plotted as a function of time. This may be contrasted with an exemplary received signal in the transmission mode, shown on the same time scale in FIG. 7. The first returning signal 202 in the reflection mode comes from the soft tissue directly below the transducer. Later arriving signals are seen to have a lower frequency content than the first arriving reflections. The late arriving signal 204 is almost exclusively determined by propagation through the underlying bone. In FIG. 8, the bone signal 206 has been isolated from the received transmission signal of FIG. 7.

After the bone signal is isolated from the "main bang" and from the tissue signal, a Fourier transform is performed to determine the frequency content of the bone signal. The result depends, of course, on the frequency content of the signal emitted by the transmitting transducer. The transmitted signal amplitude could, for example, be independent of frequency—i.e., flat. In that case, according to the Rayleigh scattering model the frequency dependence of the received signal voltage would be of the form $$V(\omega) = V^* \exp(-\alpha^* L^* \omega^4) \qquad (208)$$

where $\omega$ is the radial frequency, L the total path length through the bone, and a is the damping factor. A second form of transmitted signal is that of a ramp in frequency. The received signal would then be of the form $$V(\omega) = V^* \omega^* \exp(-\alpha^* L^* \omega^4) \qquad (210)$$

The ramp form has been found to be advantageous with respect to the analysis of the received signal. Equation (210) is that of an exponential decay with the key information contained in the decay constant α; the path length, L, is known.

Unlike the transmission mode, however, in the reflection mode, the path length through the bone, L, is not a simple, measurable constant; scatterers at varying depths cause a series of echoes. For each part of the returning signal, the path length can be inferred, however, from transit time. That is, the thickness of the soft tissue can be readily approximated and the propagation velocity in the soft tissue is well known (i.e., about 1540 m/sec.); additionally, the total propagation time from emission of the pulse to reception of the echo is known. Consequently, the path length can be correlated with the transit time as the echoes are received.

Figure 9:
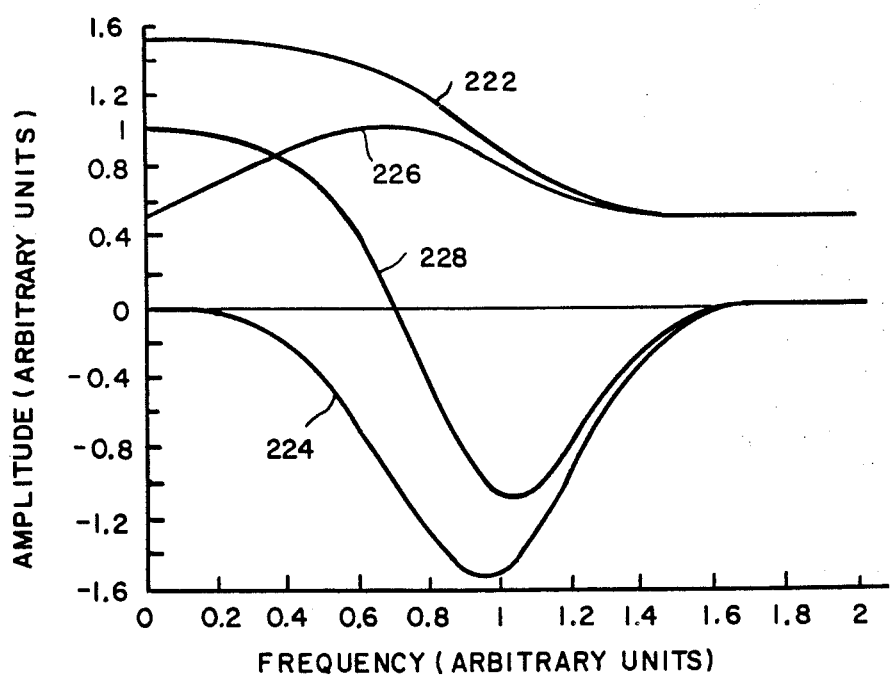
FIG. 9 is an illustration comparing the shapes calculated for received signals and their first derivatives produced in accordance with the present invention, for transmitted signals of two different wave shapes.

FIG. 9 shows how the spectral characteristics of the transmitted signal affect the received signal, assuming the bone is a Rayleigh scattering medium. When the transmitted pulse has a flat spectrum, the received signal is calculated to have the shape shown in curve 222, which is the sum of an exponentially damped response as in equation 208 plus a constant background, or leakage, signal. The background signal makes the determination of the damping constant α more difficult. However, this waveform may be differentiated, producing the curve 224. Location of the minimum of curve 224 can then be used to determine the value of α. When the transmitted pulse has a "ramp"-like spectrum (i.e., its amplitude is linear in frequency), the received signal is calculated to have the form shown in curve 226 with the same background or leakage signal present. This waveform may be differentiated, producing the curve 228. The zero crossing of the differentiated signal occurs at $\omega_{max}$ and may be used to identify $\omega_{max}$ and, consequently, α.

A third mode of operation is the scattering mode, wherein a sending transducer is used in conjunction with a receiving transducer. Unlike the transmission mode, the transducers can be placed in any non-parallel orientation with respect to each other, even at right angles.

Referring now to FIGS. 7 and 10–16, the results of empirical tests are shown for operation in the modes discussed above. These drawing figures show actual experimental results, which may or may not be representative.

Figure 7:
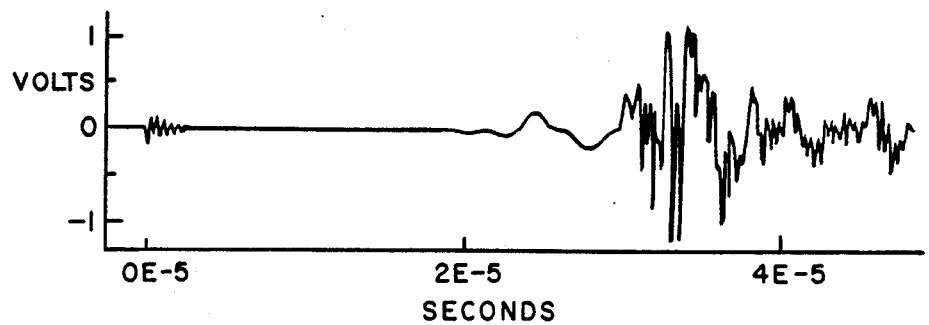
FIG. 7 is an illustrative example of the received signal according to the present invention when the invention is operated in the transmission mode to evaluate a patella.
Figure 8:
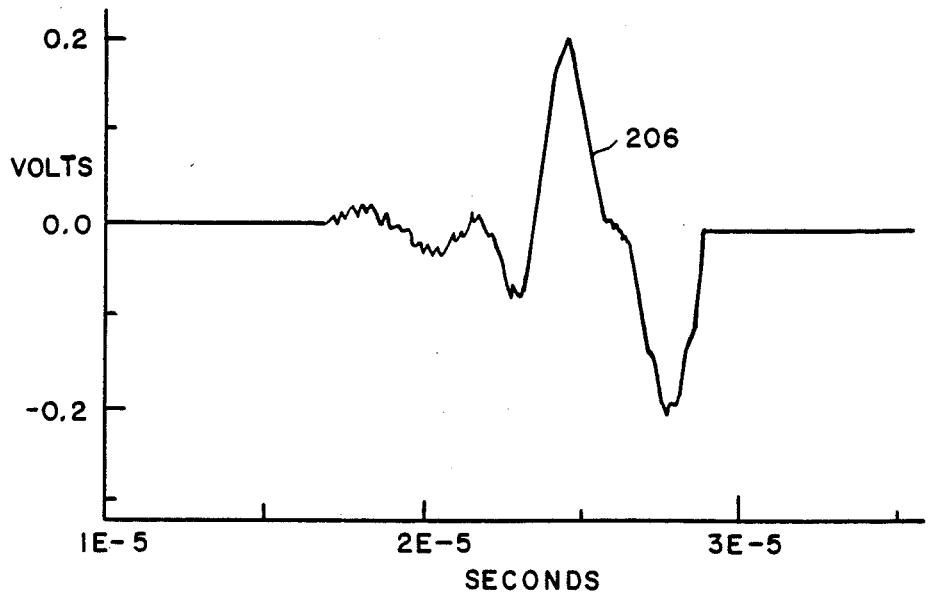
FIG. 8 is an illustration of the bone signal as extracted from the remainder of the waveform of FIG. 7.

FIG. 7 shows the signal received in the transmission mode from a patient's patella, in response to the emission of the signal of FIG. 2. Using matched filtering, the transmission contributed by the bone can be extracted; this signal 206 is shown in FIG. 8. By contrast, FIG. 6 shows the received signal in the reflection mode, for the same signal emitted into the same patella. Note the strong echo 202 which returns in the neighborhood of $10^{-6}$ seconds due to the reflection of incident energy at the soft tissue/bone interface.

Figure 10:
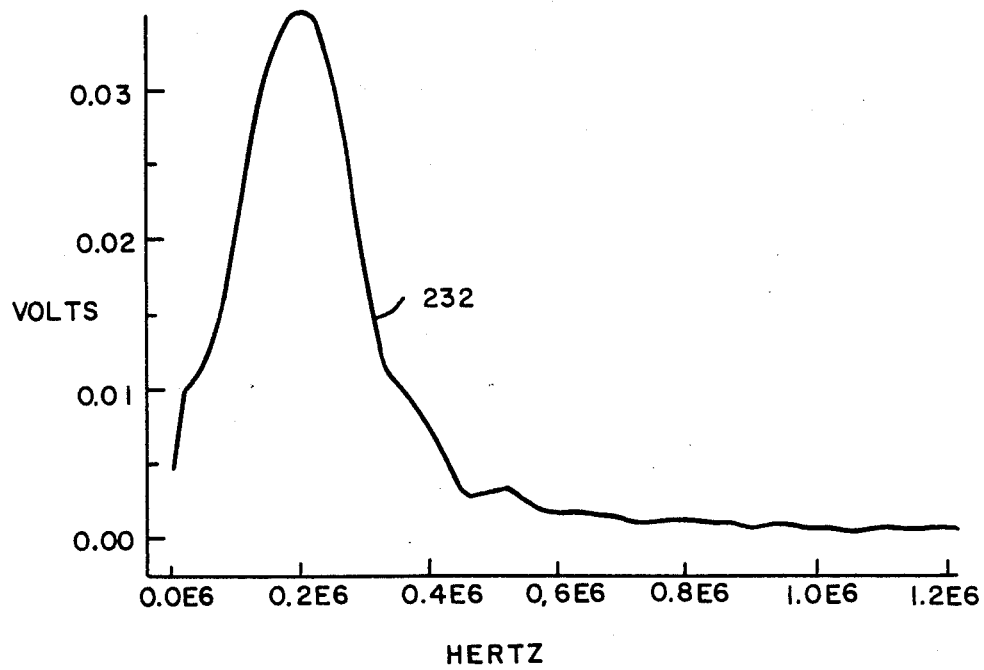
FIG. 10 is an illustration of the magnitude of the Fourier transform for an exemplary received signal, produced in the transmission mode, for a normal patella, according to the present invention.
Figure 11:
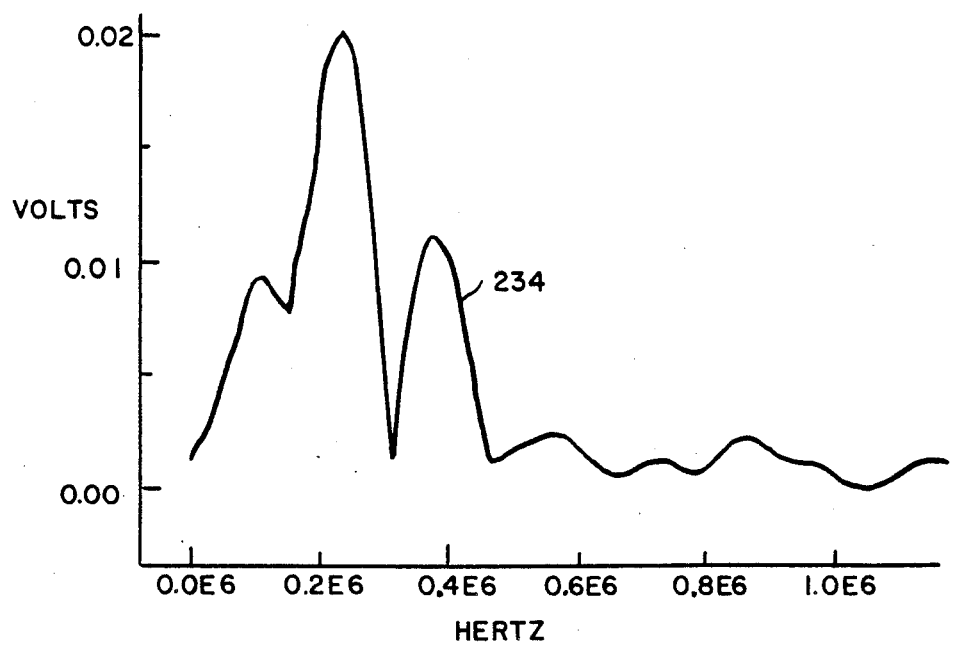
FIG. 11 is an illustration of the magnitude of the Fourier transform for an exemplary received signal, produced in the reflection mode, for a subject patella, according to the present invention.
Figure 12:
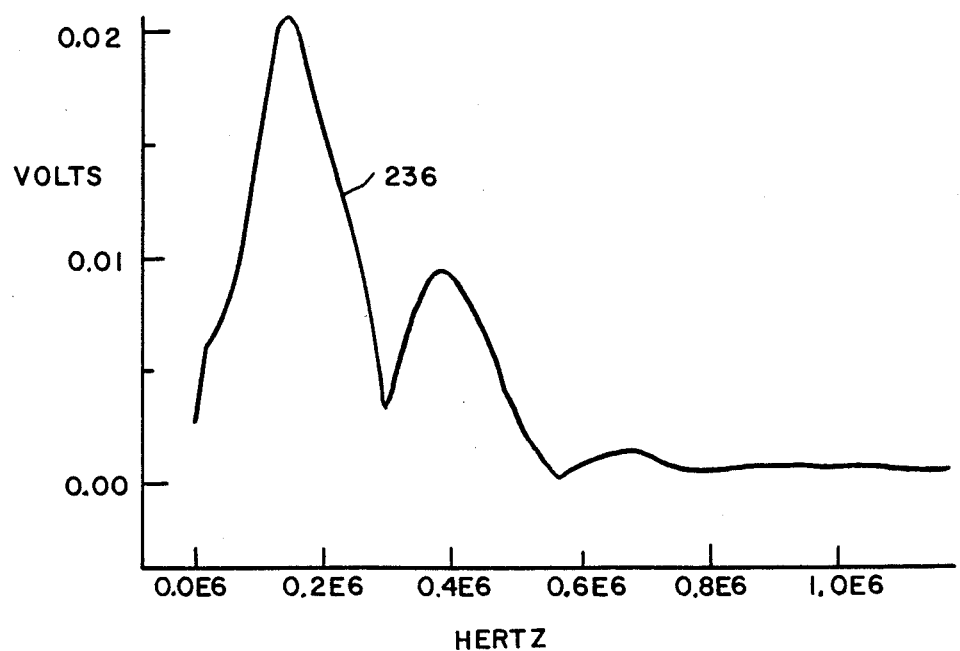
FIG. 12 is an illustration of the magnitude of the Fourier transform for an exemplary received signal, produced in the transmission mode, for an osteoporotic patella, according to the present invention.

An example of the amplitude of the Fourier transform of the received signal in the transmission mode, for a patella, using the excitation of FIG. 2, is shown in FIG. 10. The received signal 232 exhibits a maximum at 190.43 kHz and the full width of the peak at half maximum (FWHM) is 195.31 kHz. By contrast, an example of the amplitude of the Fourier transform of the received signal in the reflection mode is shown at 234 in FIG. 11. The signal 234 exhibits a peak at 239.26 kHz and the FWHM is 109.86 kHz. Another received signal from a patella transmission is shown at 236 in FIG. 12; this example shows a peak at 156.25 kHz and a FWHM of 156.25 kHz, as well. The patient in FIG. 10 has normal bone condition, while the patient in FIG. 12 is osteoporotic.

Figure 13:
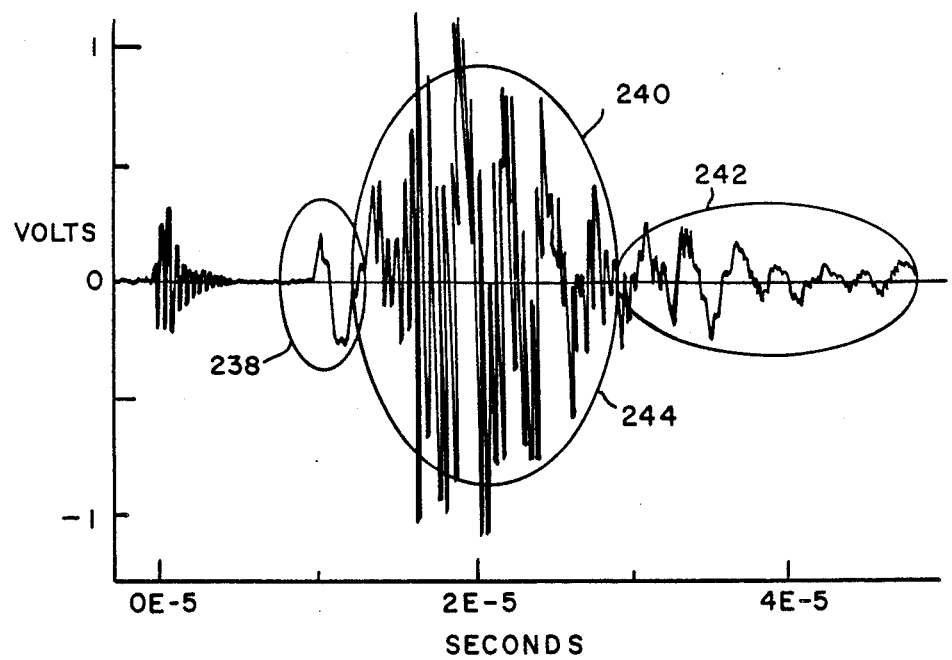
FIG. 13 is an illustration of an exemplary received signal produced in the scattering mode, for the osteoporotic patella of FIG. 12, according to the present invention.
Figure 14:
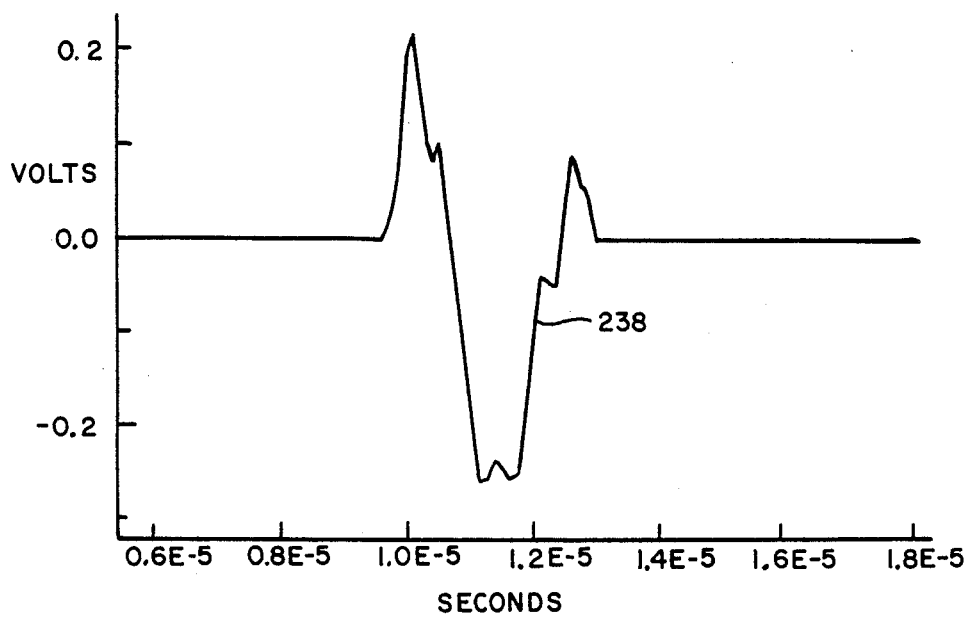
FIG. 14 is an illustration showing the initial low frequency portion of the scattering mode received signal of FIG. 13 isolated from the remainder of the received signal.
Figure 15:
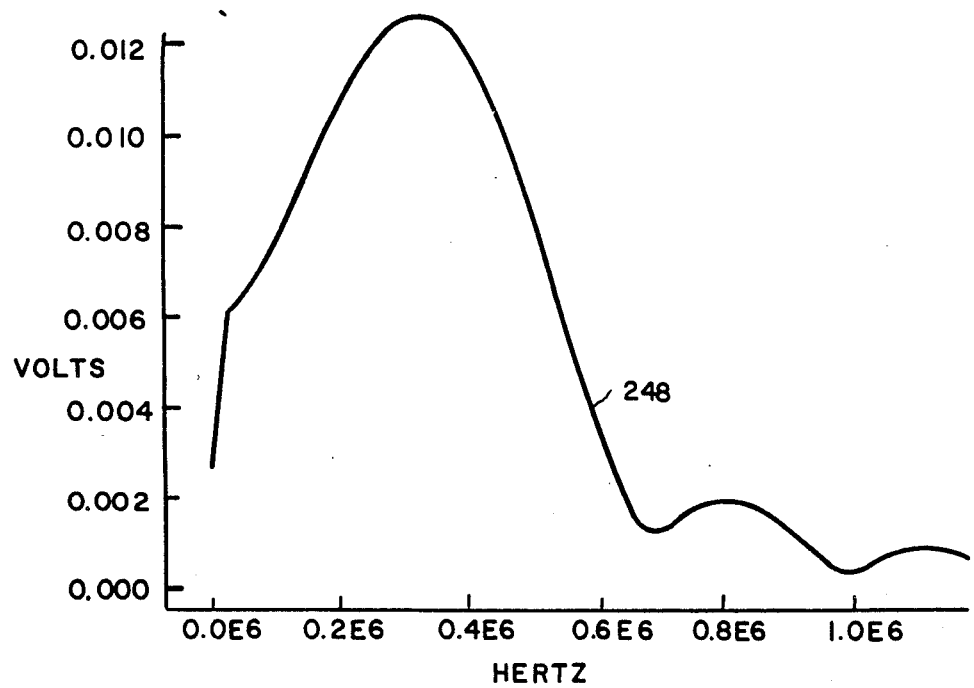
FIG. 15 is an illustration of the magnitude of the Fourier transform of the waveform of FIG. 14.
Figure 16:
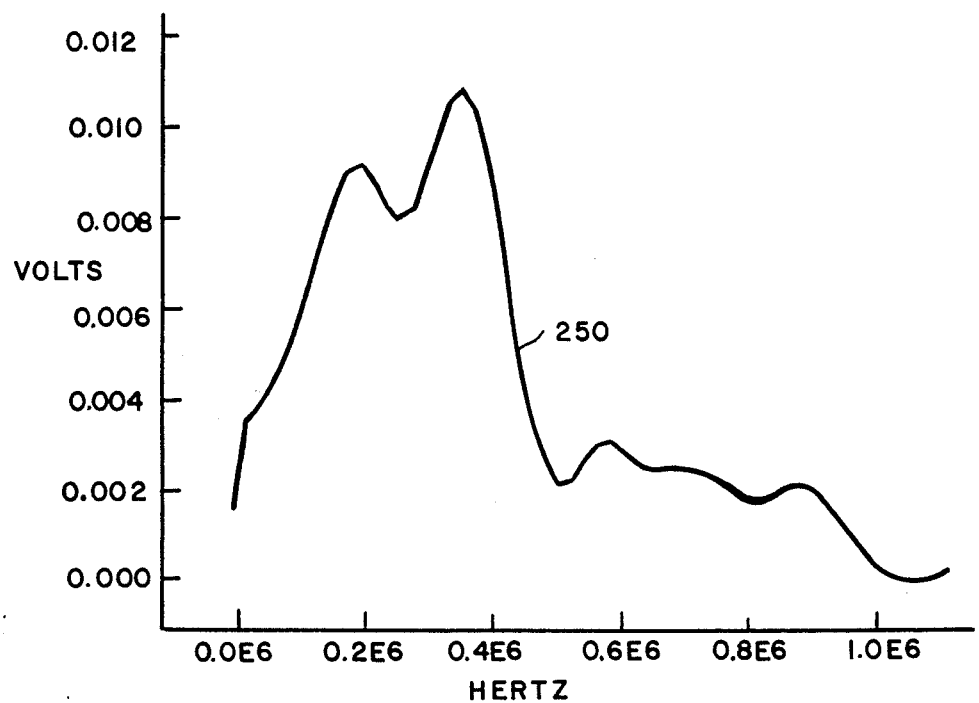
FIG. 16 is an illustration showing the magnitude of the Fourier transform of the signal from 37.2 microseconds to 51.1 microseconds in FIG. 13.

An empirical example of a received scattering mode signal is shown in FIG. 13 for a patella. The relatively low frequency component 238 which arrives early is believed to be due to "head wave" activity. The direct wave scattered response appears next, at 240. This is followed by reflections from scattering sites deep within the bone, at 242. The early-arriving low frequency signal 238 may be isolated from the composite signal 244 using conventional signal processing techniques; the low frequency signal as thus isolated is shown in FIG. 14. A Fourier transform of the signal 238 is shown at 248 in FIG. 15. The amplitude of the Fourier transform shows a main peak at 312.5 kHz with the FWHM being 410 kHz, with lesser trailing peaks (i.e., lobes). This curve closely resembles that to be expected from a head wave. When the bone signal from 37.5 us to 51.1 us is isolated and a Fourier transform is generated from that signal, the resulting amplitude waveform is shown at 250 in FIG. 16. The transform 250 has peaks at 195 kHz and 351 kHz and the FWHM=312.5 kHz. These characteristics are clear indicators of scattering.

In results believed to be reasonably representative of the performance the invention can provide, a group of 28 women were studied; half were known osteoporotics and half were known to have normal, non-osteoporotic bones. The patients were measured at the patella, using the transmission mode. The parameters used in the bone condition model included the bone/tissue velocity ratio, kurtosis, skewness, first and second moments, area, and peak frequency. A patient was declared to be osteoporotic for experimental evaluation when the probability of osteoporosis found by the present invention was greater than fifty percent. Using this criteria, 26 of the 28 patients were diagnosed correctly. Other parameters or combinations of parameters may prove to be better predictors, such as other moments, the FWHM, and so forth. Routine experimentation with a larger population, in fact, may produce a single bone condition model containing sufficient data on a large number of patients of known condition as to be statistically reliable in most instances to provide the basis for a diagnosis of a patient.

Numerical values are assigned to each descriptive parameter for each patient. Thus, if eight parameters are used, then the data for each patient corresponds to a single representative point in a parameter space of eight dimensions in which each descriptor is assigned its appropriate value along its own separate coordinate axis. If representative points associated with osteoporotic patients can be identified as being substantially different from those of the normal patients, then the points representing the osteoporotic individuals will group or cluster in a region of the parameter space recognizable different from the cluster of representative points for the normal patients. Multivariable discriminant analysis is used to determine the optimum boundary surface in parameter space so that those representaive points on one side of the boundary belong to one patient classification and those on the other side belong to another classification. The distance from a given representative point to the boundary determines the probability that the classification is correct.

A statistical model of a normal or osteoporotic patient can be constructed by collecting representative points for each group and determining through discriminant analysis the boundary between the groups. At that point, an individual patient of unknown bone condition can be assigned a probability of belonging to the normal or osteoporotic group on the basis of the location in parameter space of the representative point for the patient. The parameters that make up the representative point for the patient may include the nature of the propagation of ultrasound through the patient's bone and or other tissues as well as age, sex, race, height, weight, and other relevant parameters. The statistical model may exhibit more detailed grouping than simply to establish normal and osteoportic groups. Such further groupings can be identified by the technique of cluster analysis, wherein the representative points for a statistically significant sample of patients is examined to identify such further groupings caused by other disorders of the bone such as osteomalacia. See, for example, "Statistical Methods for Digital Computers" edited by Enslein, Ralston, and Wilf. Vol. III. John Wiley, 1977, ISBN 0-471-70690-6 (v. 3).

The foregoing description of the method should be taken as illustrative and not limiting. The kneecap has been identified as the preferred testing site of the human body for the evaluation of trabecular bone and diagnosis or monitoring of osteoporosis. The tibia provides useful results in examining compact bone. Tibial results with respect to observing osteoporosis are limited to some extent, because the tibia is largely made up of cortical bone, rather than trabecular bone. Therefore, the effects of osteoporosis are not felt as early in the tibia as in trabecular bones, such as the kneecap and the spinal cord. Further, although the method has been described in connection with diagnosing osteoporosis, it may also be used to diagnose other bone conditions. For example, it may be used to diagnose periodontal bone loss which contributes to periodontal disease, and to assess the healing of fractures.

The invention is also applicable to evaluation of animal bone conditions, but the frequency spectrum of the applied acoustic excitation may have to be varied to adjust to the animal. It may also be desirable to modify the frequency spectrum when evaluating conditions other than osteoporosis. Various other alterations, modifications and improvements will thus be obvious and will occur to those skilled in the art. Moreover, the invention may be useful also for invasive testing of bones. For this purpose, transducer tipped needles may be placed in direct contact with a bone to be studied. When this is done, of course, there is no need to make adjustments for soft tissue.

The foregoing detailed description of embodiments of the invention are presented by way of example only. Various alterations, modifications, enhancements and improvements to those embodiments are intended to occur and will be obvious to those skilled in the art. The invention is therefore intended to be limited only by the following claims and equivalents thereto.

What is claimed is:

1. A method of assessing the condition, in a subject patient, of a bony member which may be surrounded by soft tissue, such method comprising the steps of:
   a. launching into the patient proximate the surface of the bony member an ultrasound pulse signal having components in a range from at least about 100 kHz to about 600 kHz;
   b. receiving from the bony member ultrasound energy in said range and generating electrical signal (termed "received signals") corresponding to said received ultrasound energy;
   c. extracting from the received signals a plurality of parameter values characterizing the received signals; and
   d. performing a multivariable analysis on said parameter values, such analysis comparing the parameter values against the statistical distributions for such parameters in patients of known bone condition, and providing a probability that the condition of the bony member of the subject patient matches the known bone condition.

2. The method of claim 1 wherein the multivariable analysis is a multivariable discriminant analysis.

3. The method of claim 1 or claim 2 wherein the step of receiving includes receiving ultrasound energy transmitted through the bony member from a first region of the surface thereof to a second region of the surface thereof.

4. The method of claim 1 or claim 2 wherein the step of receiving includes receiving ultrasound energy reflected from within the bony member.

5. The method of claim 1 or claim 2 wherein the step of launching includes directing the ultrasound signal at the surface of the bony member so as to permit, in the receiving step, receiving ultrasound energy scattered out of the incident ultrasound signal.

6. A method of assessing the condition, in a subject patient, of a bony member which may be surrounded by soft tissue, such method comprising the steps of:
   a. launching into the patient proximate the surface of the bony member an ultrasound pulse signal having components in a range from at least about 100 kHz to about 600 kHz;
   b. receiving from the bony member ultrasound energy in said range and generating electrical signal (termed "received signals") corresponding to said received ultrasound energy;
   c. extracting from the received signals values for a plurality of parameters characterizing the architecture of the bony member; and
   d. performing a multivariable discriminant analysis on said parameter values, such analysis comparing the parameter values against the statistical distributions for such parameters in patients of known bone condition, and providing a probability that the condition of the bony member of the subject patient matches the known bone condition.

7. The method of claim 6 wherein the parameters characterizing the architecture of the bony member model the bony member as a Rayleigh scattering medium.

8. For use in connection with the diagnosis of bone condition of a patient, the method of compiling statistical information regarding the architecture of bone as a function of bone condition, such method comprising the steps of:
   a. for each of a plurality of patients, collecting data by
      1. launching into the patient proximate a selected surface of a selected bony member an ultrasound pulse signal having components within the range of about 100 kHz to about 600 kHz,
      2. receiving from the bony member ultrasound energy in said range and generating electrical signal (termed "received signals") corresponding to said received ultrasound energy, and 3. extracting from the received signals values for a plurality of parameters characterizing the architecture of the bony member; and b. associating said parameter values with the condition of the patients's bone, for each patient, such bone condition being independently known from other information.

9. The method of claim 8 wherein the ultrasound energy received from the bone is transmitted through the bony member.

10. The method of claim 8 wherein the ultrasound energy received from the bone is reflected from within the bony member.

11. The method of claim 8 wherein the ultrasound energy received from the bone is scattered from within the patient.

12. The method of any of claims 8–11 wherein the parameter values are selected from the group including the peak frequency of the received signals, the full width of the received signals at half maximum, and the first through fourth moments of the fourier transform of the bone signal.

13. The method of any of claims 8–11 wherein the parameter values are selected to characterize the bone as a Rayleigh scattering medium.

14. A method of assuring proper acoustic coupling between a transducer and a bony member in a system for assessing the condition, in a subject patient, of a bony member which may be surrounded by soft tissue, such method comprising the steps of:
  a. by means of a transducer, launching into the patient proximate the surface of the bony member an ultrasound signal having components in a spectrum from at least about 100 kHz to about 600 kHz;
  b. by means of a transducer, receiving from the bony member ultrasound energy in said spectrum and generating electrical signal (termed "received signals") corresponding to said received ultrasound energy; and
  c. computing the area under the magnitude of the received signals and comparing said area with a threshold value to generate an indication whether the received signals are reproducibly reliable for diagnosing condition of the bony member.

15. A method of assessing the condition, in a subject patient, of a bony member which may be surrounded by soft tissue, such method comprising the steps of:
  a. launching into the patient at a first position proximate the surface of the bony member an ultrasound pulse signal having components in a range from at least about 100 kHz to about 600 kHz;
  b. proximate a second position on the surface of said bony member, monitoring ultrasound energy in said range and generating electrical signal (termed "received signals") corresponding to said monitored ultrasound energy;
  c. extracting from the received signals a plurality of parameter values characterizing the received signals; and
  d. performing a multivariable discriminant analysis on said parameter values, such analysis comparing the parameter values against the statistical distributions for such parameters in patients of known bone condition, and providing a probability that the condition of the bony member of the subject patient matches the known bone condition.

16. The method of claim 15 wherein the parameter values characterizing the received signals are selected from the group comprising the area, width at half power, and peak frequency of the power spectrum of the received signal.

17. The method of claim 15 wherein the parameter values characterizing the received signals are selected from the group comprising the second, third and fourth moments of the power spectrum of the received signal.

18. The method of claim 15 wherein the parameter values characterizing the received signals include functions of the second, third and fourth moments of the power spectrum of the received signal.

19. The method of claim 18 wherein the functions include skewness and kurtosis.

20. The method of claim 15 wherein the parameter values characterizing the received signals are further selected from among the group including the ratio of the velocity of the bone signal to the velocity of the soft tissue signal.

21. The method of claim 15 wherein the parameter values characterizing the received signals include a function of the velocity of the bone signal.

* * * * *